United States Patent [19]

Yoshikawa et al.

[11] 4,060,421
[45] Nov. 29, 1977

[54] COMBINED REVERSIBLE AQUEOUS COLLOIDAL DENTAL IMPRESSION MATERIAL

[76] Inventors: Ikuji Yoshikawa, 1198, Iwato, Komae, Tokyo; Yoshihisa Noro, 71-16, Narashinodai 4-chome, Funabashi, Chiba; Junji Okaneya, No. 204, 35-14, Satsukigaoka 1-chome, Chiba, Chiba, all of Japan

[21] Appl. No.: 688,591

[22] Filed: May 21, 1976

[30] Foreign Application Priority Data

Dec. 16, 1975  Japan .................................. 50-149713

[51] Int. Cl.$^2$ ............................................... C08L 5/12
[52] U.S. Cl. .................................. 106/38.5 D; 106/35; 106/208; 106/209; 106/213; 106/214; 106/287 SB
[58] Field of Search ............... 106/35, 38.5 D, 38.5 R, 106/287 SB, 38.23, 208, 209, 213, 214

[56] References Cited

U.S. PATENT DOCUMENTS

| 2,234,383 | 3/1941 | Preble .............................. 106/38.5 D |
| 2,824,811 | 2/1958 | Erickson et al. ................ 106/38.5 D |
| 3,462,384 | 8/1969 | Kokoszka et al. .................... 106/213 |

*Primary Examiner*—Lorenzo B. Hayes
*Assistant Examiner*—Elizabeth A. Hatcher
*Attorney, Agent, or Firm*—Schmidt, Johnson, Hovey & Williams

[57] ABSTRACT

A combined reversible aqueous colloidal dental impression material comprising powdery agar-agar, water soluble starch, silicone oil, potassium sulfate, borax, perfume, pigment antiseptic and water.

A process for preparing a combined reversible colloidal dental impression material by which powdery agar-agar, water soluble starch, silicone oil potassium sulfate, borax, perfume antiseptic and pigment are admixed under heating and agitation in the presence of water and the obtained mixture is homogenized.

7 Claims, No Drawings

COMBINED REVERSIBLE AQUEOUS COLLOIDAL DENTAL IMPRESSION MATERIAL

BACKGROUND OF THE INVENTION

This invention relates to a dental material suitable for use in the making of impressions from which false or artificial teeth and fillings for decayed teeth are prepared in the field of prosthesis dentistry and more particularly to a dental material suitable for use in the making of combined impressions from which false or artificial teeth and fillings for decayed teeth are prepared and a process for preparing the dental material.

A great variety of dental materials for making impressions for preparing artificial teeth and fillings for decayed teeth are commercially available, but the conventional dental materials used for such purposes have their respective inherent advantages and disadvantages and can not individually satisfy all of the dental requirements necessary for making impressions from which artificial teeth and fillings for decayed teeth are prepared.

Aqueous colloidal dental impression materials, dental plaster and silicone dental impression materials, for example, are at present commercially available. Out of the commercially available dental impression materials referred to above, the dental plaster and silicone dental impression materials generally have a low resilience and therefore, after the material has been applied and allowed to solidify on a tooth or teeth under dental treatment the dental impression which remains in the material when the solidified dental impression material is removed from the tooth or teeth, if the tooth or teeth have any undercut or undercuts, a portion or portions of the obtained impression has to be destroyed or when applied to the corona dentis, the impression material flows over the corona dentis resulting in inaccurate impressing of the shape raised portion or portions of the crown in the dental impression material. In spite of these disadvantages, since dental plaster and silicone dental impression materials are suitable for use in the preparation of all types of dental impressions within certain limits, these dental impression materials are especially suitable for the preparation of edentulous jaw impressions and have been widely employed as the materials for the so-called complete denture impressions.

On the other hand, aqueous colloidal dental impression materials which have a high resilience are suitably employed in precise reproduction of the shape of teeth having undercuts and teeth having clearances therebetween. Although the aqueous colloidal dental impression materials can be also employed in the preparation of edentulous jaw impressions, the aqueous dental colloidal impression materials have been most suitably and widely employed in the making of partial tooth impressions such as those for metal jacket crowns, bridged false or artificial teeth, removable partial denture and fillings.

After the aqueous colloidal dental impression material has been applied and allowed to solidify on a tooth or teeth under dental treatment to provide a pattern after the shape of the tooth or teeth, when the solidified impression is removed from the tooth or teeth, even if the tooth or teeth have an undercut or undercuts, the impression material can be easily removed from the tooth or teeth because the impression resiliently deforms by virtue of its inherent resilience and immediately after the removal of the impression material from the tooth or teeth, the impression resiliently restored to its original shape. Thus, the aqueous colloidal dental impression material has the advantage that the material can provide dental impressions which precisely conform to the shape of a tooth or teeth or a portion of the tooth or teeth the shape of which is to be reproduced or patterned after. However, the aqueous colloidal dental impression materials take a rather long time to solidify and a patient whose tooth or teeth is receiving dental treatment has to wait until the dental impression solidifies without moving his jaws which is uncomfortable to the patient. In the preparation of a tooth impression, it is desirable to relieve a patient of discomfort and at the same time, to prepare a dental impression having a shape precisely conforming to the shape of the tooth under dental treatment by placing the dental impression material on a tray by the employment of an injector, rapidly picking the material up from the tray, applying the material on or about the tooth, allowing the material to solidify in position and taking the solidified impression out of the patient's mouth without plastic deformation.

For the purpose, the so-called combined impression process has been developed. According to the combined impression process, a first dental impression material is first injected onto or about a tooth the shape of which is reproduced or patterned in the impression material in close conformity with the tooth shape and then a second dental impression material or solidifying material is applied onto the first dental impression material to rapidly cool and solidify the first dental impression material to integrally combine the first and second dental impression materials together into a unitary unit and thereafter, the thus produced combined dental impression is removed from the tooth. The material employed as the first dental impression material is of the type which having suitable resilience, can precisely reproduce the shape of a tooth having an undercut or teeth having a clearance or clearances therebetween and is capable of being removed from the tooth or teeth without difficulty. The second dental impression or solidifying material has been previously cooled to a temperature below the solidification temperature of the first dental impression material prior to the application of the second dental impression or solidifying material onto the first dental impression material to thereby accelerate the solidification of the first dental impression material. According to the combined dental impression process, even if a tooth under dental treatment has an undercut or undercuts, for example, the shape of the tooth can be precisely reproduced or patterned in the dental impression material and a patient having the tooth under dental treatment can be relieved of discomfort which was otherwise inevitable in the reproduction of the shape of the tooth in the conventional dental impression material by the prior art impression preparation processes. The combined impression preparation process has the advantage that a dental impression can be prepared having only a trifling dimensional deviation even by the employment of dental plaster slurry.

Thus, the combined impression preparation process is the most preferable dental impression preparation process, but in producing a dental impression by the employment of this process, the following severe requirements have to be observed with respect to the material to be employed. The first requirement is that the dental impression material employed is capable of precisely and rapidly reproducing the shape of a tooth having an undercut or undercuts or teeth having a clearance or clearances therebetween and has such a resilience that the dental impression material can be easily removed from the tooth or teeth the shape of which has been reproduced in the material without permanent deformation after the material has solidified. The second requirement is that the second impression material or solidifying material is capable of firmly adhering to the first dental impression material and of absorbing the heat from the first dental impression material rapidly. The third requirement is that the first dental impression material and the second dental impression or solidifying material are capable of integrating into a unitary unit. If any one or more of these requirements is not satisfied, the combined impression preparation process will encounter various difficulties. That is, the shape of a tooth or teeth can not be precisely reproduced in the obtained dental impression, the obtained dental impression can not be rapidly and easily removed from the tooth or teeth without permanent deformation and the dental impression preparation becomes impossible because the dental impression material or materials are entrapped in the narrow clearance between teeth or below an undercut or undercuts in the tooth or teeth with the result that when the obtained unitary dental impression is removed from the tooth or teeth, the solidifying material is easily separated from the underlying first dental impression material. However, dental impression materials which can satisfy all the requirements mentioned hereinabove have not been developed up to date and thus, the combined dental tooth impression preparation process has not been practically employed in spite of the beneficial advantages of the process. Reversible aqueous colloidal dental impression materials of which agar-agar is a typical member are somewhat resilient in gel state and are capable of being formed into more precise dental impressions as compared with other dental impression materials. Nevertheless, the reversible aqueous colloidal dental impression materials have been considered unsuitable as materials for combined dental impressions because the reversible aqueous colloidal dental impression materials have a low adherence to the other dental impression or solidifying material which is employed in conjunction with the colloidal or first dental impression material. Even if the adhesion property of the reversible aqueous colloidal dental impression material can be enhanced by any suitable means, the reversible aqueous colloidal dental impression materials still have the disadvantage that when dental plaster slurry is poured into the impressed recess in the obtained dental impression to produce a tooth model, the so-called "rough skin" phenomenon occurs because of the retarder of the dental plaster. As one measure for precluding the rough skin phenomenon, before the dental plaster slurry is poured into the impressed recess in the obtained dental impression, the dental impression is dipped in a setting agent solution such as a potassium sulfate solution. However, it has been found that the measure can not perfectly preclude the rough skin phenomenon.

Furthermore,, when the agar-agar dental impression material is applied to a tooth having an undercut or undercuts to pattern after the shape of a tooth or teeth, no difficulty will occur because in the preparation of a dental impression the inherent resilience of the agar-agar dental impression material allows the material to freely deform along the contour of the undercut or undercuts to some extent, but when the deformation of the dental impression material exceeds a permissible limit, the agar-agar dental impression material tends to break off or the agar-agar dental impression material has a relatively low brittleness limit value.

SUMMARY OF THE INVENTION

Therefore, one object of the present invention is to provide a reversible aqueous colloidal dental impression material which has excellent adhesiveness, which is capable of producing a precise tooth impression, which precludes the so-called "rough skin" phenomenon in a dental plaster model patterned after the shape of the tooth or teeth and which is especially suitably employed in the preparation of a combined dental impression.

Another object of the present invention is to provide a tenacious dental impression material which is capable of precisely and rapidly reproducing the shape of a tooth or teeth even when the tooth or teeth have an undercut or undercuts thereon.

Another object of the present invention is to provide a dental impression material which has excellent properties such as high thermal transmission, shape holding capability and adhesiveness to other materials which are essential for the combined dental impression material.

A further object of the present invention is to provide a dental impression material which comprises agar-agar as the main component of the reversible aqueous colloidal dental material and other additives which impart adhesiveness-to-other materials to the agar-agar and which is capable of precluding the so-called "rough skin" phenomenon on dental plaster when the dental plaster is poured into the impressed recess in a dental impression patterned after the shape of a tooth or teeth under dental treatment.

A still further object of the present invention is to provide a process for preparing the reversible aqueous colloidal dental impression.

PREFERRED EMBODIMENT OF THE INVENTION

In the dental impression material of the present invention, agar-agar is employed as the main component. According to the present invention, in order to improve the brittleness of agar-agar which is one disadvantage of the material and impart adhesiveness-to-other materials to the agar-agar to thereby preclude the rough skin phenomenon on dental plaster to be poured in the impressed recess in a dental impression patterned after the shape of a tooth or teeth by the employment of the reversible aqueous colloidal dental impression material of the present invention, the agar-agar main component is added thereto borax, water soluble starch, silicone oil, potassium sulfate, in suitable amounts for example and the components are admixed under heating whereby the borax increases the gel strength of the agar-agar and improves the brittleness of the main component on one hand and the water soluble starch and silicone oil, potassium sulfate improve the adhesiveness-to-other components of the agar-agar and preclude the rough skin on dental plaster to be employed in the preparation of a tooth model from the dental impression produced from the reversible aqueous colloidal dental impression material of the invention.

The following is one example of the blending ratio of the components in the reversible aqueous colloidal dental impression material of the present invention for ten impression.

| Component | Amount (percent) |
|---|---|
| powdery agar-agar | 8.5 – 14.0 |
| water soluble starch | 1.0 – 2.0 |
| silicone oil | 0.3 – 1.0 |
| potassium sulfate | 1.5 – 2.0 |
| borax | 0.1 – 0.2 |
| antiseptic | 0.1 – 0.2 |
| perfume | 0.1 – 0.2 |
| pigment | 0.1 – 0.2 |
| water | 79.9 – 88.3 |

The reversible aqueous colloidal dental impression material of the present invention is prepared by placing the above-listed components into a stainless container and admixing the components in the container on a hot water bath at about 85° – 90° C for about 20 minutes under agitation. The agitation-heated components form a perfect sol-state viscous mass. The sol-state viscous mass is transferred into a homogenization means and homogenized under agitation at the speed range of 8,000–15,000 R.P.M. and preferably at the speed of about 10,000 R.P.M. The homogenized sol-state viscous mass constitutes the dental impression material of the present invention. In order that the dental impression material can be easily stored and transported, the material is sucked or pumped into a pipe having a desired diameter, cooled in the pipe to solidify it and divided into ten parts to provide sticks. The thus obtained sticks can be stored for a long time by storaging the sticks under cold atmospheric conditions. When the stick is to be employed for its intended purpose by a dentist, the dental impression material stick is heated to its dissolving temperature and maintained in its solution state ready for practical use.

As the solidifying material employed in a combined dental impression formed of the tooth impression material of the present invention, an alginate impression material is most suitable, but other solidifying materials can be also employed within the scope of the present invention. As well known in the art, the alginate dental impression material accelerates the solidification of the underlying sol-state dental impression material and gives the sol-state dental impression material a shape-holding property when applied to the latter. When the alginate solidifying material is previously cooled to the gelation temperature of the material before the same is applied to the dental impression material, the solidifying material improves its cooling and solidifying action on the dental impression material.

As is clear from the foregoing description of the preferred embodiment of the present invention, it will be understood that the reversible aqueous colloidal dental impression material not only relieves dentists of tedious work such as admixing the components prior to application of the dental impression material to a tooth or teeth the shape of which is to be reproduced or patterned after and employment of a specific solidifying liquid prior to pouring of the dental plaster slurry, but also enables the dentists to perform an impression operation rapidly and precisely without giving any pain to patients whose teeth are receiving dental treatment.

While only one embodiment of the present invention has been shown and described in detail it will be understood that the same is for illustration purpose only and not to be taken as a definition the invention, reference being had for this purpose to the appended claims.

What is claimed is:

1. A reversible aqueous colloidal dental impression material emplaceable about a tooth for making an impression thereof, and which effectively bonds to an alginate solidifying material placed therearound in a combined impression process, said reversible impression material comprising:
   respective quantities of water and agar-agar;
   minor amounts of silicone oil and potassium sulfate for minimizing the formation of rough skin when said impression material is in contact with dental plaster; and
   a minor amount of water soluble starch sufficient for causing effective bonding between said impression material and said alginate solidifying material in a combined impression process.

2. The dental impression material as set forth in claim 1 wherein said starch is present at a level of from about 1.0 to 2.0%.

3. The dental impression material as set forth in claim 1 including a quantity of borax for increasing the gel strength of said impression material.

4. The dental impression material as set forth in claim 1 wherein said agar-agar is present at a level of from about 8.5 to 14.0%, said water is present at a level of from about 79.9 to 88.3%, said silicone oil is present at a level of from about 0.3 to 1.0%, said potassium sulfate is present at a level of from about 1.5 to 2.0%, and said water soluble starch is present at a level of from about 1.0 to 2.0%.

5. A method of preparing a reversible aqueous colloidal dental impression material emplaceable about a tooth for making an impression thereof, and which effectively bonds to an alginate solidifying material placed therearound in a combined impression process, said method comprising the steps of:
   admixing and heating together respective quantities of water, agar-agar, minor quantities of silicone oil and potassium sulfate, and a minor amount of water soluble starch sufficient for causing effective bonding between said impression material and said solidifying material in a combined impression process, in order to form a sol-state viscous mass; and
   homogenizing said mass.

6. The method as set forth in claim 5 including the step of cooling said homogenized mass to the solid state.

7. The method as set forth in claim 5 wherein said agar-agar is present at a level of from about 8.5 to 14.0%, said water is present at a level of from about 79.9 to 88.3%, said silicone oil is present at a level of from about 0.3 to 1.0%, said potassium sulfate is present at a level of from about 1.5 to 2.0%, and said water soluble starch is present at a level of from about 1.0 to 2.0%.

* * * * *

UNITED STATES PATENT OFFICE
CERTIFICATE OF CORRECTION

Patent No. 4,060,421               Dated November 29, 1977

Inventor(s) Ikuji Yoshikawa et al.

It is certified that error appears in the above-identified patent and that said Letters Patent are hereby corrected as shown below:

On the cover sheet insert:

-- (73) Assignee: Tetsuji Okaneya and Ikuji Yoshikawa, both of Tokyo, Japan, part interest each --

Signed and Sealed this

Twenty-seventh Day of June 1978

[SEAL]

Attest:

RUTH C. MASON
Attesting Officer

DONALD W. BANNER
Commissioner of Patents and Trademarks